United States Patent
Parten

(10) Patent No.: US 8,460,439 B2
(45) Date of Patent: Jun. 11, 2013

(54) METHOD FOR CONTROLLING BUTANOL CONCENTRATION IN FERMENTATION BROTH

(75) Inventor: William D. Parten, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 261 days.

(21) Appl. No.: 12/747,926

(22) PCT Filed: Dec. 12, 2008

(86) PCT No.: PCT/US2008/086568
§ 371 (c)(1),
(2), (4) Date: Jun. 14, 2010

(87) PCT Pub. No.: WO2009/079362
PCT Pub. Date: Jun. 25, 2009

(65) Prior Publication Data
US 2010/0279370 A1 Nov. 4, 2010

Related U.S. Application Data

(60) Provisional application No. 61/007,665, filed on Dec. 14, 2007.

(51) Int. Cl.
*B01D 19/00* (2006.01)
(52) U.S. Cl.
USPC .............. 95/254; 95/258; 95/263; 261/117

(58) Field of Classification Search
USPC ............. 435/160, 161, 162, 313, 319, 290; 252/182.12; 95/241, 254, 258, 263; 261/117
See application file for complete search history.

(56) References Cited

U.S. PATENT DOCUMENTS

| | | | | |
|---|---|---|---|---|
| 1,759,122 A | * | 5/1930 | Lichtenthaeler | 435/161 |
| 4,336,335 A | * | 6/1982 | Muller et al. | 435/161 |
| 4,802,975 A | * | 2/1989 | Mehlberg | 208/390 |
| 2008/0220488 A1 | * | 9/2008 | D'Amore et al. | 435/157 |
| 2009/0155869 A1 | * | 6/2009 | Buelter et al. | 435/160 |

FOREIGN PATENT DOCUMENTS

| | | |
|---|---|---|
| AU | 620802 | 10/1988 |
| JP | 3249917 | 11/1991 |
| JP | 2005052685 | 3/2005 |

OTHER PUBLICATIONS

Groot, et al., Batch and Continuous Butanol Fermentations with Free Cells: Integration with Product Recovery by Gas-stripping, Appl. Microbiol. Biotechnol. 32:305-308, 1989.
Qureshi, et al., Recovery of Butanol from Fermentation Broth by Gas Stripping, Renewable Energy 22:557-564, 2001.
Roffler, et al., In-situ Recovery of Butanol during Fermentation, Bioprocess Eng. 2:1-12, 1987.

* cited by examiner

*Primary Examiner* — Robert A Hopkins
(74) *Attorney, Agent, or Firm* — Christine M. Lhulier

(57) ABSTRACT

The present invention relates to a two stage process to control the butanol concentration from fermentation broth.

22 Claims, 4 Drawing Sheets

METHOD FOR CONTROLLING BUTANOL CONCENTRATION IN FERMENTATION BROTH

CROSS-REFERENCE TO RELATED APPLICATIONS

This application claims benefit of priority from Provisional Application No. 61/007,665, filed Dec. 14, 2007.

FIELD OF THE INVENTION

The present invention relates to a two stage process involving stripping and absorption to remove butanol from fermentation broth.

BACKGROUND

There is much interest in converting fermentable renewable sources of carbon to other useful chemicals, such as, but not limited to fuel or fuel additives or specialty or commodity chemicals.

Currently, much industrial fermentation involves the manufacture of ethanol for either chemical or fuel use. However, there is advantage to producing butanol by fermentation. For use in fuel, butanol is superior to ethanol, namely butanol has lower vapor pressure and decreased solubility in water. Hence, it would be desirable to have an economical fermentation process by which butanol could be obtained.

An advantageous butanol fermentation process would encompass a complete, or substantially complete, conversion of sugars to butanol without reaching a butanol titer that causes the rate of butanol production to fall below an undesirable predetermined rate (the "tolerance level", usually influenced by economic considerations). One way of achieving this goal is to limit sugar loadings to a level whereby batch fermentation does not result in butanol titers that cause the rate of butanol production to fall below the predetermined rate. However, this approach is undesirable because limited sugar loadings result in dilute solutions that are economically undesirable to process. Therefore, there is a need for a process that achieves the aforementioned goal in a way that does not require a limitation on sugar loading.

One means by which a butanol-producing fermentation process might be made more efficient would be to continuously remove butanol from the fermentation medium (broth), so that the tolerance level of the butanol producing microorganism is not reached. This should allow high loadings of sugar to be charged to the fermentation vessel, allowing favorable economics to be achieved. Such a removal process, when associated with fermentation, is generally termed an "In situ Product Removal" process, or an "ISPR" process for short. For an ISPR process to be useful, it needs to be integrated with, compatible with, or easily segregated from, the fermentation process itself. For example, simple distillation of the fermentation broth at atmospheric pressure would not be useful as an ISPR technique because the fermentation microorganisms would most likely be damaged by the temperature in the base of the distillation column.

The present invention represents a means by which In situ Product Removal (ISPR) can be successfully carried out to control butanol concentrations in fermentation broth at or below the tolerance level of the fermentation microorganism. Hence, the current invention is believed to enable butanol fermentation to be carried out using a microorganism, concentrations of sugars and other nutrients which result in favorable economics.

The present invention provides an ISPR process which solves the problem of toxic butanol levels which can destroy a microorganism in a fermentation process by ensuring that butanol concentration in a fermentation broth can be maintained below the tolerance level of the fermentation microorganisms and allowing for subsequent recycle of the fermentation microorganisms back to the fermentation vessel consequently enhancing the efficiency of the process.

SUMMARY OF THE INVENTION

Figure 1:
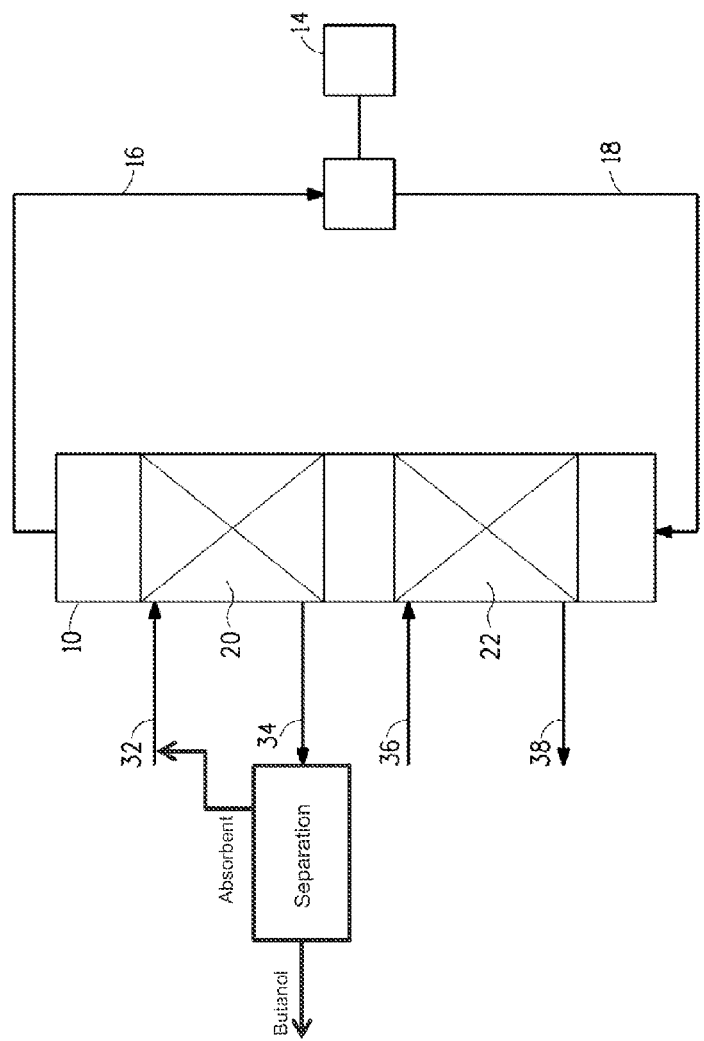
FIG. 1 shows an apparatus having stripping and absorption sections for removing butanol from a fermentation broth, where the fermentation broth is contacted counter-currently by the stripping gas.

A method for controlling the concentration of butanol at or below a predetermined level in one or more fermentation broths comprising butanol and water and contained in one or more respective fermentation vessels, said method comprising:

(a) continuously removing a portion of at least one of the fermentation broths from its respective fermentation vessel to form a removed fermentation broth;

(b) feeding the removed fermentation broth into a stripping section of an apparatus in which said stripping section is in gaseous communication, but not liquid communication, with an associated absorption section, the apparatus having at least one stripping section with an associated absorption section;

(c) simultaneously feeding an inert gas into the stripping section, thereby causing a portion of the butanol to leave the fermentation broth and form (i) a gaseous mixture comprising butanol and the inert gas and (ii) a reduced-butanol fermentation broth;

(d) returning the reduced-butanol fermentation broth to its respective fermentation vessel, and allowing the gaseous mixture to enter the absorption section of the apparatus that is associated with the stripping section of step (b);

(e) continuously feeding into the absorption section of step (d) an organic liquid absorbent having a lower vapor pressure than that of butanol and an ability to absorb butanol, thereby forming a liquid mixture comprising the liquid absorbent and at least a portion of the butanol from the gaseous mixture, thereby reducing the butanol content in the gaseous mixture to form a reduced-butanol gaseous mixture;

(f) returning the reduced-butanol gaseous mixture to a stripping section of the apparatus;

(g) recovering butanol from the liquid mixture and returning the liquid absorbent to an absorption section of the apparatus;

thereby, as a result of the method, controlling the concentration of butanol in the fermentation broth.

Another embodiment provides the process, wherein removal from the same fermentation vessel is simultaneous for two or more fermentation broth streams.

Another embodiment provides the process, wherein removal of the two or more fermentation broth streams is non-simultaneous.

In yet another embodiment, the process, wherein removal from different fermentation vessels is simultaneous for two or more fermentation broth streams.

In yet another embodiment, the process, wherein removal from different fermentation vessels is non-simultaneous for two or more fermentation broth streams.

Another embodiment provides the process, wherein removal from different fermentation vessels is separate for two or more fermentation broth streams.

Another embodiment provides the process, wherein the inert gas is nitrogen.

In yet another embodiment, the process, wherein the inert gas is air.

In yet another embodiment, the process, wherein the inert gas is $CO_2$.

In yet another embodiment, the process, wherein the stripping apparatus is located inside the fermentation vessel.

Another embodiment provides the process, wherein the stripping apparatus is located exterior to the fermentation vessel.

Another embodiment provides the process, wherein the organic liquid absorbent is a $C_8$ or higher alcohol.

In yet another embodiment, the process, wherein the alcohol is selected from the group consisting of octanol, nonanol, and decanol and mixtures thereof.

In yet another embodiment, the process, wherein the alcohol is decanol.

Another embodiment provides the process, wherein the butanol is recovered by distillation.

In yet another embodiment, the process wherein recovery of butanol is selected from the group consisting of absorption, liquid-liquid extraction and crystallization.

An embodiment provides a method for recycling at least one fermentation broth comprising fermentation microorganisms from a fermentation process wherein butanol is produced in at least one fermentation vessel, said method comprising:
(a) removing a portion of the fermentation broth comprising fermentation microorganisms wherein said butanol is produced from its respective fermentation vessel to form a removed fermentation broth comprising fermentation microorganisms;
(b) feeding the removed fermentation broth comprising fermentation microorganisms into a stripping section of an apparatus in which said stripping section is in gaseous communication, but not liquid communication, with an associated absorption section, the apparatus having at least one stripping section with an associated absorption section;
(c) simultaneously feeding an inert gas into the stripping section, thereby causing a portion of the butanol to leave the removed fermentation broth comprising fermentation microorganisms and form (i) a gaseous mixture comprising butanol and the inert gas and (ii) a reduced-butanol fermentation broth comprising fermentation microorganisms; and
(d) returning the reduced-butanol fermentation broth comprising fermentation microorganisms to its respective fermentation vessel.

In yet another embodiment, wherein physical loss of fermentation broth microorganism and sugars is less than 1%.

Another embodiment provides the process, wherein the inert gas is nitrogen.

In yet another embodiment, the process, wherein the inert gas is $CO_2$.

An embodiment provides an intermediate composition comprising a butanol-rich absorbent phase comprising about 5% to about 15% butanol and an organic liquid absorbent having a lower vapor pressure than butanol.

In yet another embodiment, the composition, wherein the liquid absorbent is a $C_8$ or higher alcohol.

In yet another embodiment, the composition, wherein the alcohol is selected from the group consisting of octanol, nonanol, decanol and mixtures thereof.

In yet another embodiment, the composition, wherein the alcohol is decanol.

DETAILED DESCRIPTION

As used above and throughout the description of the invention, the following terms, unless otherwise indicated, shall be defined as follows:

"In Situ Product Removal" as used herein means the selective removal of a specific fermentation product from a biological process such as fermentation to control the product concentration in the biological process.

"Counter-currently" as used herein refers to the internal arrangement of process streams within a unit operation that can be divided into several sub sections by which the process streams flow in opposite directions to each other. In particular in this application the stripping and absorbing sections in the contacter will have liquid put to the top of the section which will flow down through gravity and vapor introduced into the bottom of the section and will flow up through pressure gradient.

"Co-currently" as used herein refers to the internal arrangement of process streams within a unit operation that can be divided into several sub sections by which the process streams flow in the same direction as each other. In particular in this application the stripping and absorbing sections in the contacter will have liquid put to the top of the section which will flow down through gravity and vapor will also be introduced into the top of the section and will flow down through pressure gradient. This is opposite to the normal arrangements.

"Butanol" as used herein means 1-butanol, 2-butanol, isobutanol, and mixtures thereof.

"Inert Gas" as used herein means a gas that does not interact with the process of fermentation and has low solubility in the both the fermentation broth and the absorbent. The inert gas may be a mixture of compounds that might include but not be limited to $N_2$ and $CO_2$.

"Fermentation broth" as used herein means the mixture of water, sugars, dissolved solids, suspended solids, microorganisms producing butanol, product butanol and all other constituents of the material held in the fermentation vessel in which product butanol is being made by the reaction of sugars to butanol, water and $CO_2$ by the micro organisms present.

"Fermentation vessel" as used herein means the vessel in which the fermentation reaction by which product butanol is made from sugars is carried out.

"Stripping" as used herein means the action of transferring all or part of a volatile component from a liquid stream into a gaseous stream.

"Stripping section" as used herein means that part of the contacting device in which the stripping operation takes place.

"Gaseous communication" as used herein means a gaseous phase that is a product from one piece of equipment or operation is then passed to a second piece of equipment or operation to which it is in communication.

"Liquid communication" as used herein means that a liquid phase that is a product from one piece of equipment or operation is then passed to a second piece of equipment or operation to which it is in communication.

"Absorption" as used herein means the action of transferring all or part of a component from a gaseous stream into a liquid stream.

"Absorption section" as used herein means the part of the contacting device in which the absorption operation takes place.

"Reduced-butanol fermentation broth" as used herein means material that has a similar composition to the fermentation broth but has been acted upon in such a way to preferentially reduce the composition of the butanol in the material.

"Concentration of butanol" as used herein means the amount of butanol contained within a stream compared to the amount of the whole stream.

"Absorbent" as used herein means a liquid that is able to absorb another species from a gas phase. Such as for example this may be heavy a alcohol that is then able to absorb butanol from a gaseous phase.

The fermentation of sugar to butanol produces two other products: a mole of water per mole of sugar, and two moles of $CO_2$. Typically, in a batch fermentation, the water that is made remains in the fermentation vessel, while the $CO_2$ is vented as a gas. A small amount of the butanol will also be vented with the $CO_2$, but at the temperatures of the fermentation, the rate of butanol removal is small compared to its production rate.

The current invention is generally described below with reference to FIG. 1 through FIG. 4.

The current invention consists of a two stage ISPR process of stripping and absorption to remove butanol from the fermentation broth. The operating conditions, including temperatures and pressures, of the stripping operation of the ISPR process are similar to those used in the fermentation vessel, enabling the viability of the fermentation microorganism. In the first stage, butanol is stripped from the fermentation broth in a stripping unit by a gas stream comprising an inert carrier gas. The inert carrier gas can comprise nitrogen, $CO_2$, air, or mixtures thereof. The inert carrier gas can further comprise at least one additional gas so long as the presence of the additional gas is not deleterious to the process. The selection of the inert carrier gas can be based on availability and cost, for example.

The volatility of butanol under these conditions is much greater than water and hence an increase in the concentration of butanol in the gas stream, relative to water, will occur. The rate of stripping needs to be such that butanol levels in the fermentation vessel are maintained at or below the tolerance level. The amount of carrier gas required at the temperature of the fermentation is much greater than the amount of $CO_2$ that is given off by the fermentation process, consequently, a source of carrier gas will be required. This stripping process could take place in the fermentation vessel itself, but is more likely carried out outside of this vessel in an external stripping unit. The liquid resulting from the stripping process is returned to the fermentation vessel where the microorganisms can continue to convert unused sugar to butanol, $CO_2$ and water. Physical loss of the microorganism and sugars from the fermentation broth as a result of the stripping process should be minimal, for example less than about 1%, because of their low volatilities. The stripping process is operated in such a manner that it is not deleterious to the microorganism and the sugars in the fermentation broth. Meanwhile, the butanol-containing carrier gas stream is passed to an absorption unit where it is contacted with a low volatility organic absorbent, having a lower vapor pressure than that of butanol, such as an ether, aldehyde, ester, ketone, or alcohol, preferably an alcohol having eight or more carbon atoms, for example octanol, nonanol, or decanol, and mixtures thereof, wherein the butanol is preferentially absorbed from the carrier gas to form a butanol-rich absorbent phase. A butanol rich absorbent phase is one where the butanol content is about 5% to 15%.

The butanol-rich absorbent phase is then processed by means known in the art for example distillation, absorption, liquid-liquid extraction, crystallization) to regenerate a substantially butanol-free absorbent for reuse in the absorption unit and to produce a product butanol stream. The resulting carrier gas stream from the absorption process is low in butanol content and can be recycled to the front of the process (the stripping unit) by use of suitable mechanical compression equipment, such as a fan, blower, or compressor, thereby forming a gas loop. If $CO_2$ is the preferred carrier gas, the $CO_2$ generated from the reactor can be introduced into the gas loop, with excess $CO_2$ in the loop being purged from the remainder of the process via a suitable scrubbing system.

FIG. 1, depicts an apparatus for carrying out an embodiment of the present invention. Such apparatus can be purchased from commercial vendors or assembled by one skilled in the art. The apparatus comprises a column 10 that includes an absorption section 20 and a stripping section 22. Typically, sections 20 and 22 will comprise trays or packing, as is well known in the art. In addition, gas exits at or near the top of column 10 via line 16 and is raised in pressure by mechanical compression equipment 14, such as a fan, blower or compressor, and is returned to, or near to, the bottom of column 10 via line 18. Maintenance of sufficient gas in the system is controlled by purge or make-up in a conventional manner (not shown). The process is operated by passing fermentation broth from a fermentation vessel (not shown) via line 36 into, or near to, the top of stripping section 22, wherein the broth is then contacted counter-currently by gas entering column 10 via line 18. A fraction of the butanol contained in the fermentation broth is transferred into the gas and is passed from the top of the stripping section 22 to the bottom of the absorption section 20, resulting in a stripped fermentation broth that is formed in section 22. The stripped fermentation broth is returned to the fermentation vessel via line 38. Butanol that is contained in the gas passing from section 22 to section 20 is absorbed in section 20 by a low volatility organic absorbent, having a lower vapor pressure than that of butanol, such as an ether, aldehyde, ester, ketone, or alcohol, preferably an alcohol having eight or more carbon atoms, for example octanol, nonanol, or decanol, and mixtures thereof, that is introduced into the top of the absorption section via line 32 wherein the butanol is preferentially absorbed from the carrier gas to form a butanol-rich absorbent phase. A butanol rich absorbent phase is one where the butanol content is about 5% to 15%.

Butanol is removed from absorption section 20, along with the low volatility absorbent via line 34 and then separated from the low volatility absorbent using conventional separation techniques such as distillation, decantation, absorption, liquid-liquid extraction, crystallization (not shown).

An alternative embodiment to the apparatus shown in FIG. 1 is one in which the vertical relationship of the absorption and stripping sections of column 10 is reversed, i.e., the stripping section 22 resides above the absorption section 20.

Figure 2:
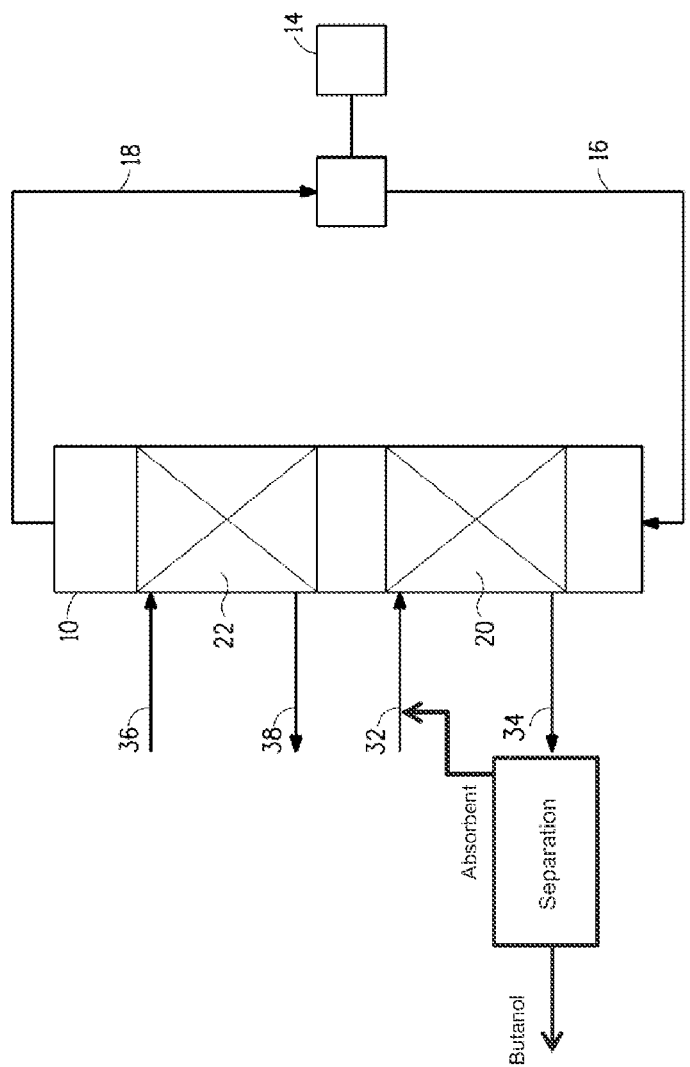
FIG. 2 shows an apparatus having stripping and absorption sections for removing butanol from a fermentation broth, where the fermentation broth is contacted co-currently by the stripping gas.

FIG. 2 depicts an apparatus for carrying out a further embodiment of the present invention. The apparatus comprises a column 10 that includes an absorption section 20 and a stripping section 22. Typically, sections 20 and 22 will comprise trays or packing, as is well known in the art. In addition, gas exits at or near the bottom of column 10 via line 16 and is raised in pressure by mechanical compression equipment 14, such as a fan, blower or compressor, and is returned to, or near to, the top of column 10 via line 18. Maintenance of sufficient gas in the system is controlled by purge or make-up in a conventional manner (not shown).

The process is operated by passing fermentation broth from a fermentation vessel (not shown) via line 36 into, or near to, the top of the stripping section 22, wherein the broth is then contacted co-currently by gas entering column 10 via line 18. A fraction of the butanol contained in the fermentation broth is transferred into the gas and is passed from the bottom of the stripping section 22 to the top of the absorption section 20, resulting in a stripped fermentation broth that is formed in section 22. The stripped fermentation broth is returned to the fermentation vessel via line 38. Butanol that is contained in the gas passing from section 22 to section 20 is absorbed in section 20 by a low volatility organic absorbent, having a lower vapor pressure than that of butanol, such as an ether, aldehyde, ester, ketone, or alcohol, preferably an alcohol having eight or more carbon atoms, for example octanol, nonanol, or decanol, and mixtures thereof, that is introduced into the top of the absorption section via line 32 wherein the butanol is preferentially absorbed from the carrier gas to form a butanol-rich absorbent phase. A butanol rich absorbent phase is one where the butanol content is about 5% to 15%. Butanol is removed from the absorption section 20, along with the low volatility absorbent via line 34 and then separated from the low volatility absorbent using conventional separation techniques such as distillation, decantation, absorption, liquid-liquid extraction, crystallization (not shown).

An alternative embodiment of the apparatus shown in FIG. 2 is one in which the vertical relationship of the absorption and stripping sections of column 10 is reversed, i.e., the absorption section 20 resides above the stripping section 22.

Figure 3:
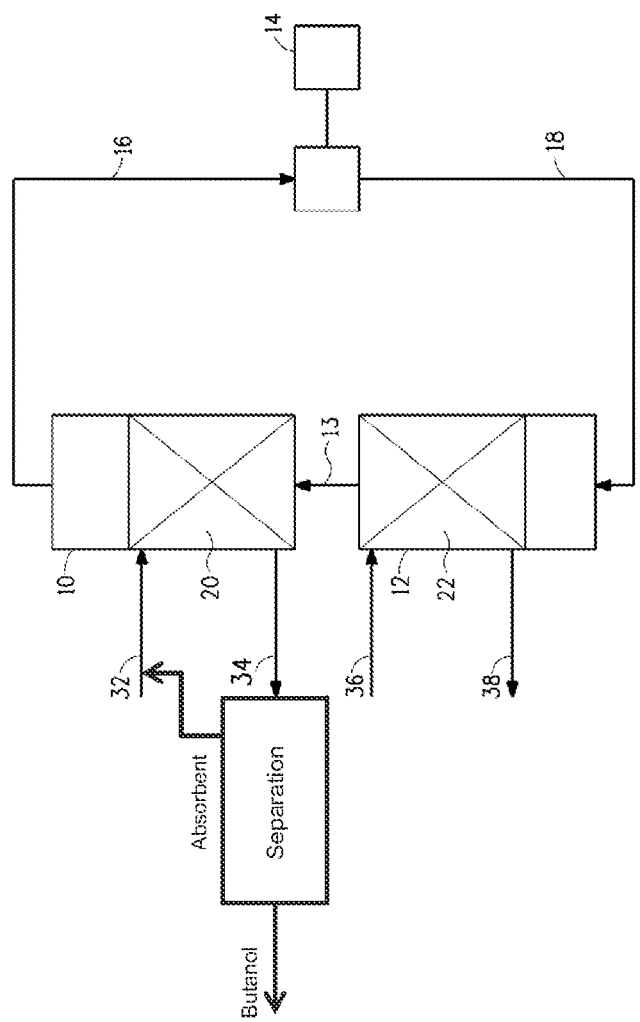
FIG. 3 shows an apparatus having a column having a stripping section and a column having an absorption section for removing butanol from fermentation broth.

FIG. 3, depicts an apparatus for carrying out a further embodiment of the present invention. The apparatus comprises a column 10 containing absorption section 20 and column 12 containing stripping section 22. Typically, sections 20 and 22 will comprise trays or packing, as is well known in the art. The columns are connected via line 13 by which gas can pass from the top, or near the top, of column 12 to the bottom, or near the bottom, of column 10. In addition gas exits at or near the top of column 10 via line 16 and is raised in pressure by mechanical compression equipment 14, such as a fan, blower or compressor, and is returned to, or near to, the bottom of column 12 via line 18. Maintenance of sufficient gas in the system is controlled by purge or make-up in a conventional manner (not shown).

The process is operated by passing fermentation broth from a fermentation vessel (not shown) via line 36 into, or near to, the top of the stripping section 22, wherein the broth is then contacted counter-currently by gas entering column 12 via line 18. A fraction of the butanol contained in the fermentation broth is transferred into the gas and is passed from the top of the stripping section 22 to the bottom of the absorption section 20 via line 13, resulting in a stripped fermentation broth that is formed in section 22. The stripped fermentation broth is returned to the fermentation vessel via line 38. Butanol that is contained in the gas passing from section 22 to section 20 is absorbed in section 20 by an organic absorbent having a lower vapor pressure than that of butanol, such as an ether, aldehyde, ester, ketone, or alcohol, preferably an alcohol having eight or more carbon atoms, for example octanol, nonanol, or decanol, and mixtures thereof, that is introduced into the top of the absorption section via line 32 wherein the butanol is preferentially absorbed from the carrier gas to form a butanol-rich absorbent phase. A butanol rich absorbent phase is one where the butanol content is about 5% to 15%. Butanol is removed from the absorption section 20, along with the low volatility absorbent via line 34 and then separated from the low volatility absorbent using conventional separation techniques such as distillation, decantation, absorption, liquid-liquid extraction, crystallization.

An alternative embodiment of the apparatus shown in FIG. 3 is one where the sequence of operations relative to the gas flow is reversed, i.e., from (1) stripping, then absorption, then mechanical compression to (2) absorption, then stripping, then mechanical compression.

Figure 4:
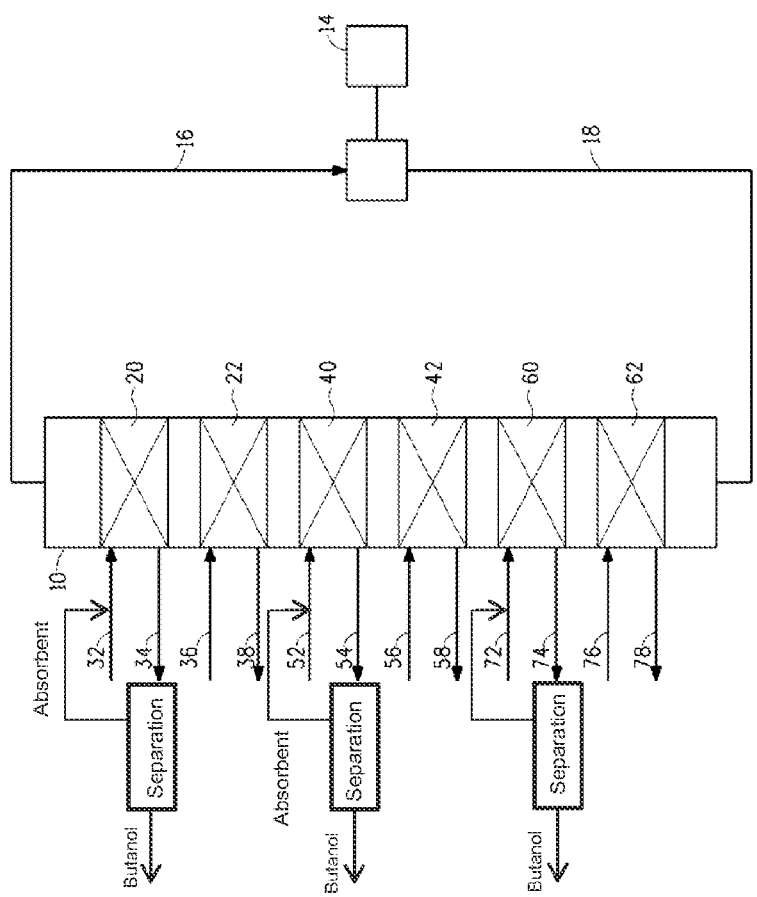
FIG. 4 shows an apparatus having a column having a series of associated pairs of stripping and absorption sections for removing butanol from fermentation broth.

Referring now to FIG. 4, there is shown apparatus for carrying out a further embodiment of the present invention. The apparatus comprises a column 10 which includes a series of associated pairs of absorption and stripping sections. In FIG. 4, three pairs of absorption and stripping sections are shown, but more or fewer are feasible. Sections 20 and 22 form an upper pair of absorption and stripping sections, respectively; sections 40 and 42 form a middle pair of absorption and stripping sections; and sections 60 and 62 form a lower pair of absorption and stripping sections. In addition gas exits at or near the top of column 10 via line 16 and is raised in pressure by mechanical compression equipment 14, such as a fan, blower or compressor, and is returned to, or near to, the bottom of column 10 via line 18. Gas will pass up column 10 passing from section 62 to section 60, from section 60 to section 42, from section 42 to section 40, from section 40 to section 22 and from section 22 to section 20. Maintenance of sufficient gas in the system is controlled by purge or make-up in a conventional manner (not shown).

The process is operated by passing fermentation broth from a fermentation vessel (not shown) via line 76 into, or near to, the top of the bottom stripping section 62 which is then contacted counter-currently by gas entering column 10 via line 18. A fraction of the butanol contained in the fermentation broth is transferred into the gas and is passed from the top of the stripping section 62 to the bottom of the absorption section 60, resulting in a stripped fermentation broth that is formed in section 62. The stripped fermentation broth is returned to the fermentation vessel via line 78. Butanol that is contained in the gas passing from section 62 to section 60 is absorbed in section 60 by a low volatility organic absorbent, having a lower vapor pressure than that of butanol, such as an ether, aldehyde, ester, ketone, or alcohol, preferably an alcohol having eight or more carbon atoms, for example octanol, nonanol, or decanol, and mixtures thereof, that is introduced into the top of the absorption section via line 72 wherein the butanol is preferentially absorbed from the carrier gas to form a butanol-rich absorbent phase. A butanol rich absorbent phase is one where the butanol content is about 5% to 15%. Butanol is removed from the absorption section 60, along with the low volatility absorbent via line 74 and then separated from the low volatility solvent using conventional separation techniques such as distillation, decantation, absorption, liquid-liquid extraction, crystallization.

In like manner, the process can be operated by passing fermentation broth simultaneously from the same vessel or different fermentation vessels (not shown) to the middle and upper stripping section/absorption section pairs.

By stacking stripping section/absorption section pairs to operate in series, the diameter of the column can be reduced, although the height will be increased. The volume of $CO_2$ or other inert gas circulated will be reduced, although at the expense of having to compress over a higher pressure ratio. In a process where multiple fermentation vessels are operating, it is likely to be advantageous to keep the streams of fermentation broth separate, which can be facilitated by having multiple stripping section/absorption section pairs.

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specification, as indicating the scope of the invention.

What is claimed is:

1. A method for controlling the concentration of butanol at or below a predetermined level in one or more fermentation broths comprising butanol and water and contained in one or more respective fermentation vessels, said method comprising:
   (a) continuously removing a portion of at least one of the fermentation broths from its respective fermentation vessel to form a removed fermentation broth;
   (b) feeding the removed fermentation broth into a stripping section of an apparatus in which said stripping section is in gaseous communication, but not liquid communication, with an associated absorption section, the apparatus having at least one stripping section with an associated absorption section;
   (c) simultaneously feeding an inert gas into the stripping section, thereby causing a portion of the butanol to leave the fermentation broth and form (i) a gaseous mixture comprising butanol and the inert gas and (ii) a reduced-butanol fermentation broth;
   (d) returning the reduced-butanol fermentation broth to its respective fermentation vessel, and allowing the gaseous mixture to enter the absorption section of the apparatus that is associated with the stripping section of step (b);
   (e) continuously feeding into the absorption section of step (d) an organic liquid absorbent having a lower vapor pressure than that of butanol and an ability to absorb butanol, thereby forming a liquid mixture comprising the liquid absorbent and at least a portion of the butanol from the gaseous mixture, thereby reducing the butanol content in the gaseous mixture to form a reduced-butanol gaseous mixture;
   (f) returning the reduced-butanol gaseous mixture to a stripping section of the apparatus; and
   (g) recovering butanol from the liquid mixture and returning the liquid absorbent to an absorption section of the apparatus;
   thereby, as a result of the method, controlling the concentration of butanol in the fermentation broth.

2. The process of claim 1, wherein removal from the same fermentation vessel is simultaneous for two or more fermentation broth streams.

3. The process of claim 1, wherein removal of the two or more fermentation broth streams is non-simultaneous.

4. The process of claim 1, wherein removal from different fermentation vessels is simultaneous for two or more fermentation broth streams.

5. The process of claim 1, wherein removal from different fermentation vessels is non-simultaneous for two or more fermentation broth streams.

6. The process of claim 4 or 5, wherein removal from different fermentation vessels is separate for two or more fermentation broth streams.

7. The process of claim 1 wherein the inert gas is nitrogen.

8. The process of claim 1, wherein the inert gas is $CO_2$.

9. The process of claim 1, wherein the stripping apparatus is located inside the fermentation vessel.

10. The process of claim 1, wherein the stripping apparatus is located exterior to the fermentation vessel.

11. The process of claim 1, wherein the organic liquid absorbent is a $C_8$ or higher alcohol.

12. The process of claim 11, wherein the alcohol is selected from the group consisting of octanol, nonanol, and decanol and mixtures thereof.

13. The process of claim 12, wherein the alcohol is decanol.

14. The process of claim 1, wherein the butanol is recovered by distillation.

15. The process of claim 1, wherein recovery of butanol is selected from the group consisting of absorption, liquid-liquid extraction and crystallization.

16. A method for recycling at least one fermentation broth comprising fermentation microorganisms from a fermentation process wherein butanol is produced in at least one fermentation vessel, said method comprising:
   (a) removing a portion of the fermentation broth comprising fermentation microorganisms wherein said butanol is produced from its respective fermentation vessel to form a removed fermentation broth comprising fermentation microorganisms;
   (b) feeding the removed fermentation broth comprising fermentation microorganisms into a stripping section of an apparatus in which said stripping section is in gaseous communication, but not liquid communication, with an associated absorption section, the apparatus having at least one stripping section with an associated absorption section;
   (c) simultaneously feeding an inert gas into the stripping section, thereby causing a portion of the butanol to leave the removed fermentation broth comprising fermentation microorganisms and form (i) a gaseous mixture comprising butanol and the inert gas and (ii) a reduced-butanol fermentation broth comprising fermentation microorganisms; and
   (d) returning the reduced-butanol fermentation broth comprising fermentation microorganisms to its respective fermentation vessel.

17. The process of claim 16, wherein the inert gas is nitrogen.

18. The process of claim 16, wherein the inert gas is $CO_2$.

19. An intermediate composition comprising a butanol-rich absorbent phase comprising about 5% to about 15% butanol and an organic liquid absorbent having a lower vapor pressure than butanol.

20. The composition of claim 19, wherein the liquid absorbent is a $C_8$ or higher alcohol.

21. The composition of claim 20, wherein the alcohol is selected from the group consisting of octanol, nonanol, decanol and mixtures thereof.

22. The composition of claim 20 or 21, wherein the alcohol is decanol.

* * * * *